United States Patent [19]

Farkas et al.

[11] Patent Number: 5,340,823
[45] Date of Patent: Aug. 23, 1994

[54] ORGANOSILANE DERIVATIVES, PHARMACEUTICAL COMPOSITIONS CONTAINING THEM AND PROCESS FOR PREPARING SAME

[75] Inventors: Sandor Farkas, Budapest; Sandor Földeak, Szeged; Egon Karpati, Budapest; Peter Hegyes, Szeged; Janos Kreidl, Budapest; Laszlo Szporny, Budapest; Laszlo Czibula, Budapest; Szilvia Petüfi-Vass, Szeged, all of Hungary

[73] Assignee: Richter Gedeon Vegyeszeti Gyar RT., Budapest, Hungary

[21] Appl. No.: 993,139

[22] Filed: Dec. 18, 1992

Related U.S. Application Data

[62] Division of Ser. No. 736,962, Jul. 29, 1991, Pat. No. 5,198,446.

[30] Foreign Application Priority Data

Jul. 27, 1990 [HU] Hungary .................. 4647/90

[51] Int. Cl.$^5$ .................. A61K 31/445; C07D 7/10
[52] U.S. Cl. .................. 514/317; 514/239.5; 514/255; 514/330; 514/383; 514/396; 514/399; 514/408
[58] Field of Search .................. 544/69; 546/14; 548/110; 514/228.8, 231.2, 247, 239.5, 255, 277, 315, 330, 359, 383, 396, 399, 408

[56] References Cited

U.S. PATENT DOCUMENTS

| | | | |
|---|---|---|---|
| 4,224,317 | 9/1980 | Barcza | 546/14 |
| 4,762,826 | 8/1988 | Eckhardt | 514/63 |
| 5,198,446 | 3/1993 | Farkas | 514/277 |

FOREIGN PATENT DOCUMENTS 3805117  8/1989  Fed. Rep. of Germany.

Primary Examiner—Celia Chang
Attorney, Agent, or Firm—Herbert Dubno; Jonathan Myers

[57] ABSTRACT

A method of treating a mammalian subject for Parkinson's disease or to provide a central muscle relaxant effect, which comprises the step of administering to the mammalian subject in need of the treatment, a therapeutically effective amount of a compound of the Formula (I)

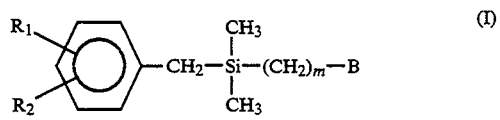

wherein
m is 1,2 or 3;
$R_1$ and $R_2$ each independently stand for hydrogen, $C_1$ to $C_4$ straight or branched chain alkyl, $C_1$ to $C_4$ alkoxy, $C_5$ to $C_7$ cycloalkyl, or halogen; and
B is a 5- or 6-membered saturated or unsaturated heterocyclic group containing a nitrogen heteroatom, the heterocyclic group being bound through its heterocyclic nitrogen atom to the remainder of the compound, and which can contain one or two additional heteroatoms selected from the group consisting of an oxygen heteroatom, a sulfur heteroatom, and one or two additional nitrogen heteroatoms, which may be as an =N—, —NH— or —NR— group, where R is a $C_1$ to $C_5$ alkyl or $C_1$ to $C_5$ alkycarbonyl group, the nitrogen-containing heterocyclic group is unsubstituted or substituted on one of its carbon atoms by $C_1$ to $C_4$ alkyl or $C_1$ to $C_4$ alkoxycarbonyl; or a pharmaceutically acceptable salt thereof.

3 Claims, No Drawings

ORGANOSILANE DERIVATIVES, PHARMACEUTICAL COMPOSITIONS CONTAINING THEM AND PROCESS FOR PREPARING SAME

This is a divisional of co-pending application Ser. No. 07/736,962, filed on Jul. 29, 1991, now U.S. Pat. No. 5,198,446.

FIELD OF THE INVENTION

The invention relates to novel organosilanes of the formula

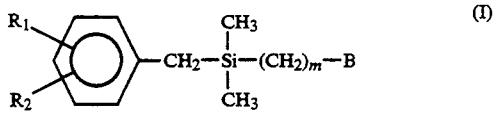

containing basic nitrogen, wherein
m is 1, 2 or 3;
$R^1$ and/or $R^2$ stand for hydrogen, a straight or branched chain $C_{1-4}$alkyl, $C_{1-4}$alkoxy, $C_{5-7}$cycloalkyl group or halogen; and
is a 5- or 6-membered saturated or unsaturated heterocyclic group, which is bound through its nitrogen atom and contains at least one nitrogen and optionally and additional oxygen, sulfur or nitrogen or an —NH or —NR group, wherein R is a $C_{1-5}$alkyl or $C_{1-5}$alkylcarbonyl group an optionally the heterocyclic group is substituted with $C_{1-4}$alkyl or $C_{1-4}$alkoxycarbonyl, as well as their acid addition salts an pharmaceutical compositions containing these compounds. Furthermore, the invention relates to a process for the preparation of the above compounds and compositions.

The novel compounds of formula (I) according to the invention are biologically active in that they exert a significant central muscle relaxant action and, on the other hand, they effectively inhibit the experimentally induced tremor used as a model of the Parkinson's disease.

In this description:
Alkyl groups as $R^1$ and/or $R^2$ may be methyl, ethyl, n- or isopropyl, n-, sec- or tert.-butyl; alkoxy groups as $R^1$ and/or $R^2$ may be methoxy, ethoxy, propoxy or butoxy; cycloalkyl groups as $R^1$ and/or $R^2$ may be cyclopentyl, cyclohexyl, or cycloheptyl. Halogen as $R^1$ and/or $R^2$ preferably is fluorine or chlorine.

As an alkylcarbonyl group, R may mean methyl-, ethyl-, propyl-, butyl- or pentylcarbonyl group; as an alkyl group, R may be methyl, ethyl, propyl, butyl or pentyl.

BACKGROUND OF THE INVENTION

Organosilane-type compounds are commonly known. The types of these compounds described up to the present are very diversified and the number of the specifically characterized compounds is high. Some therapeutical effects or organosilanes have also been published.

Aminoalkylsilanes used for the treatment of Parkinson's disease due to their monoamine oxidase-inhibiting effect are described e.g. in the European patent specification No. 291,781.

N-heterocyclic compounds used for the preparation of pesticides and discussed in the European patent specification No. 224,024, may be considered to be structurally related to the compounds of formula (I).

Fungicidally active nitrogen-containing organosilane derivatives are also known (Latv. PSR Zinat. Akad. Vestis, Kim. Ser. 1978, pp. 343-349).

DESCRIPTION OF THE INVENTION

Surprisingly, it has been found that the novel organosilane derivatives of the formula (I) containing basic nitrogen, wherein $R^1$, $R^2$, B and m are as defined above, possess significant muscle relaxant properties. Thus, being central muscular relaxants, the compounds of Formula (I) are useful for treating symptoms such as spastic or rigid muscular hypertonicity of various origins as well as Parkinson's disease and syndrome.

This action was studied by using methods indicating the central muscle relaxant effect as well as the experimental model of Parkinson's disease. The compounds according to the invention were compared on the basis of test results to tolperisone and eperisone as reference drugs showing a similar activity profile.

The methods used and results of our investigations are discussed hereinafter.

Method 1: Test based on the GYKI-20039-induced tremor

Groups consisting of 10 to 20 male CFLP mice each weighing 19 to 21 g were intraperitoneally (i.p.) treated with 10 mg/kg of GYKI-20039 (test substance). Similarly to the structurally related compound of code number LON-954, GYKI-20039 induces a tremor on mice which is considered to be an experimental model of Parkinson's disease[Coward et al., Psychopharmacology 52, 165 (1977); Andrási et al., IX. Internat. Congress of Neuropathology, I-98, 209, Vienna (1982)]. The GYKI-20039-induced tremor usually reaches a maximum strength at 4 to 8 minutes following the administration of the test substance, thereafter it is continuously decreased and abolished within about one hour. According to our experiences made on ten known central muscle relaxants, this tremor can be inhibited by central muscle relaxants in a dose-dependent manner and it is useful for the assay (determination) of the central muscle relaxant effect.

After administration of the test substance the mice were suspended on an isometric dynamometer in a light plastic box and the strength of the tremor was measured and quantified by electronic integration. The tremor strength of mice was averaged in the 4th-5th minutes following the treatment with 10 the test substance.

The animals were pretreated with various doses of the muscle relaxants to be tested before administration of the test substance. The time of pretreatment was 0 in intravenous examinations, whereas a pretreatment time of 10 minutes was used in oral investigations. The $ED_{50}$ value, i.e. the dose causing 50% inhibition, was determined from the logarithmic dose-response curve by linear regression. The arithmetic mean of the integrated activity values of the group treated with the test substance or the untreated control group, respectively was considered to be the inhibition of 50%.

Method 2: Straub's tail test

The method of Novack [Drug Development Res. 2, 383 (1982)] was used with some modification. Groups consisting of 10 male OF-1 mice each weighing 19 to 21 g were intraperitoneally treated with 60 mg/kg of morphine hydrochloride. The formation (development) of Straub's stail was judged by 15 minutes after the morphine treatment. It was considered to be positive when the animal permanently kept his tail upwards in an angle being steeper than 45°. A pretreatment was carried out with various doses of the compound to be tested by 20 minutes before the time of reading. The $ED_{50}$ value, i.e. the dose inhibiting the positive response in 50% of the animals, was calculated by using the method of Litchfield and Wilcoxon.

(The above author found a good correlation between the effectivity shown in this test method and the clinical effect of central muscle relaxants.)

Method 3: Flexor reflex on anaesthetized cats

Chloralose-anaesthetized cats of both sexes weighing 2.2 to 5.4 kg each were used in these experiments. The flexor reflex of the animals was assessed by using the quantitative electromyographic method of Farkas et al. [Pharmacol. Res. Comm. 20, Suppl. 1, 141 (1988)].

The effect of 10 mg/kg doses of the various compounds was investigated for evaluation of the strength of activity. Values calculated from the average results of 4 to 8 experiments are summarized in Table 1. For characterization of duration of the effect the time ($T_{75\%}$) is shown, which passed after administration of this dose up to the return to 75% of the control value.

The pharmacological studies showed the compounds of the invention to possess central muscle relaxant and antiparkinsonic effects. The pharmacological activity of compounds exerting the most prominent effects as well as those of tolperisone and eperisone used as reference drugs, are summarized in Table 1.

Each of the compounds appearing in Table resulted in an inhibition of 50 to 80% of the flexor reflex in the dose administered.

TABLE 1

| | Mice | | Flexor reflex on cats 10 mg/kg i.v. |
|---|---|---|---|
| Compound | GYKI-20039 $ED_{50}$ (mg/kg) i.v. | Straub's tail $ED_{50}$ (mg/kg) i.p. | Duration of effect $T_{75\%}$ (min) |
| Tolperisone | 10.2 | 63.0 | 50 |
| Eperisone | 7.8 | 63.6 | 90 |
| 2 | 2.8 | 21.8 | >180 |
| 10 | 2.8 | 22.0 | >180 |
| 19 | 3.6 | 22.3 | >180 |
| 34 | 8.7 | 30.7 | 120* |
| 35 | 3.7 | 25.9 | >180 |
| 11 | 3.8 | 27.5 | >180 |
| 12 | 5.4 | 26.9 | >180** |

Marks used in the Table 1:
*the effect of 5 mg/kg was investigated which induced an inhibition of 53%;
**the dose of 10 mg/kg investigated resulted only in an inhibition of 40%;
The numbers 2, 10, 11, 12, 19, 34 and 35 appearing in the Table are the numbers of Examples describing the preparation of the above compounds.

It is obvious from the results indicated in Table 1 that, when administered intravenously or intraperitoneally to mice, the effectivity of most of the novel compounds is 2 to 3 times as high as that of the reference drugs. On cats, their inhibitory activity on the flexor reflex was similar to that of both reference drugs, however, the duration of their effect was unexpectedly longer than the 2- to 3-fold of that of the reference drugs.

For the verification of the oral activity the tremor test was used on mice whereas the flexor reflex was investigated by using intraduodenal (i.d.) administration. The results are shown in Table 2.

TABLE 2

| | Tremor test on mice $ED_{50}$ p.o. (mg/kg) | Flexor reflex on cats | | |
|---|---|---|---|---|
| Compound | | Dose i.d. (mg/kg) | Maximum inhibition (%) | $T_{75\%}$ (min) |
| Tolperisone | 338.0 | 25 | 33.1 | 60 |
| | | 50 | 76.6 | 140 |
| Eperisone | 126.0 | 25 | 38.5 | 60 |
| | | 50 | 74.8 | 190 |
| 2* | 27.6 | 12.5 | 44.8 | 230 |
| | | 25 | 82.1 | >>300 |

*Number of the Example describing the preparation of the compound

The results shown in Table 2 indicate that, when administered to mice in the oral route, the compound No. 2 was 10 times as active as tolperisone and 5 times as active as eperisone. On intraduodenal administration to cats the half of the dose of any of both reference drugs was needed to achieve a given effect and simultaneously, the duration of effect of compound No. 2 exceeded even the duration of effect of 4-fold doses of the reference drugs.

Method 4: Study on the acute toxicity

These experiments were carried out on groups consisting of 10 male and 10 female mice each weighing 19 to 21 g. For the determination of the intravenous toxicity the substances to be tested were dissolved in 10 ml/kg of body-weight of physiological saline and injected to the tail vein of CFLP mice during 1 minute. For evaluation of the oral toxicity the substances to be tested were dissolved in 10 ml/kg of body-weight of physiological saline and introduced to the stomach of OF-1 mice by using a rigid gastric tube. The perishing ratio of the animals was evaluated by 48 hours following the administration of the substance to be tested. The $LD_{50}$ value, i.e. the dose causing the death of 50% of the animals was calculated by using the method of Litchfield and Wilcoxon. The therapeutic (safety) ratio was determined as the ratio of the $LD_{50}$ value to $ED_{50}$ value shown in the GYKI-20039-induced tremor test. The acute toxicity values and therapeutic ratios are shown in Table 3.

TABLE 3

| | Muscle relaxant effect Tremor $ED_{50}$ (mg/kg) | | Acute toxicity $LD_{50}$ (mg/kg) | | Therapeutic $LD_{50}/ED_{50}$ $LD_{50}/LD_{50}$ | |
|---|---|---|---|---|---|---|
| Treatment | i.v. | p.o. | i.v. | p.o. | i.v. | p.o. |
| 2* | 2.8 | 27.6 | 25.5 | 228 | 9.1 | 8.3 |
| Tolperisone | 10.1 | 338 | 39.8 | 612 | 3.9 | 1.8 |
| Eperisone | 7.8 | 126 | 53.4 | 320 | 6.8 | 2.5 |

*Number of the Example describing the preparation of the compound

It can be seen from the results shown in Table 3 that the therapeutic ratio of compound No. 2 is significantly more advantageous in comparison to the reference drugs both in intravenous and oral route of administration.

It is obvious from the pharmacological results that the compounds according to the invention as well as their pharmaceutically acceptable salts and particularly the compound No. 2 as one of the most effective representatives thereof possess excellent central relaxant properties in comparison to the known compounds.

The subject of the present invention is a novel group of organosilane compounds of which many members exert outstanding central muscle relaxant and anti-parkinsonic features on the basis of the pharmacological results. They surpass in many respects the commercially available muscle relaxants, their oral activity is satisfactory and the duration of their effect is long. It can be expected that depending on the body weight, age, sex and route of the administration they exert their therapeutic effect on humans in a daily dose of 5 to 500 mg.

According to an other aspect of the invention, there is provided a process for the preparation of the compounds of the formula (I) containing basic nitrogen, wherein m is 1, 2 or 3;

$R^1$ and/or $R^2$ stand for hydrogen, a straight or branched chain $C_{1-4}$alkyl, $C_{1-4}$alkoxy, $C_{5-7}$-cycloalkyl group or halogen;

B means a 5- or 6-membered saturated or unsaturated heterocyclic group, which is bound through its nitrogen atom and contains at least one nitrogen and optionally and additional oxygen, sulfur or nitrogen or an —NH or —NR group, wherein R means a $C_{1-5}$alkyl group as well as their acid addition salts, which comprises reacting a haloorganosilane compound of the formula (II),

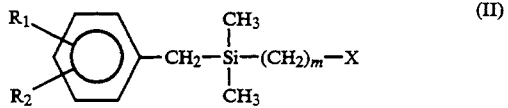

wherein $R^1 R^2$ and m are as defined above and X means halogen, or a solution thereof in an organic solvent with a 5- or 6-membered saturated or unsaturated heterocyclic compound containing at least one basic nitrogen, optionally an additional oxygen, sulfur or nitrogen atom, —NH or —NR group, wherein R means a $C_{1-5}$alkyl group and, if desired, converting the compound of formula (I) obtained to its acid addition salt.

According to the preferred embodiment of the process of the invention a haloorganosilane compound of the formula (II) is dissolved in an inert organic solvent, preferably in xylene or toluene, an above-discussed 5- or 6-membered saturated or unsaturated heterocyclic compound containing at least one basic nitrogen is added to the above solution and the mixture is refluxed. After termination of the reaction water is added to the reaction mixture and the aqueous phase obtained is separated from the organic layer. The organic layer is washed with water, then, after drying and filtering, the organic solution is evaporated to a solvent-free state.

If desired, the compounds of formula (I) obtained in the base form may be converted to their salts.

Any pharmaceutically acceptable mineral acid is suitable for the salt formation; preferably hydrochloric acid is used for this purpose. In order to enhance the water-solubility of the compounds of formula (I), e.g. fumaric acid and the like may be used as pharmaceutically acceptable salt-forming organic acids.

The crude product may be purified by distillation under reduced pressure, recrystallization or recrystallization following the formation of the hydrochloride. When the compound of formula (I) is recrystallized in the form of the base, it is suitable to use an ether-type solvent, preferably methyl tertiary butyl ether; when the recrystallization is carried out in the salt form, then it is useful to employ a mixture of an aprotic dipolar and aprotic solvent, preferably a mixture containing methyl ethyl ketone and methanol or methyl propyl ketone and isopropanol.

The starting substances used in the process according to the invention are in general known compounds. The compounds of formula (II) may be prepared by using known methods, e.g. by reacting a Grignard compound with a chlorosilane derivative. Suitably, this reaction is carried out according to the nature of the reaction under alcohol-free, anhydrous conditions with exclusion of the air in ether-type solvents and preferably in a mixture of benzene with tetrahydrofuran.

The compounds according to the invention can be converted to pharmaceutical compositions in a known manner. The pharmaceutical compositions may be administered in an oral, rectal and/or parenteral route. For the oral administration the composition may be formulated e.g. as a tablet, dragée or capsule. Lactose or starch may be used as filling materials for the preparation of oral compositions. Gelatine, carboxymethylcellulose sodium, methylcellulose, polyvinylpyrrolidone or starch gum may be used e.g. as binding or granulating materials. Potato starch or microcrystalline cellulose may be added as disintegrating agents although ultraamylopectin or formaldehyde-casein and the like may also be used. Talc, colloidal silicic acid, stearin, calcium or magnesium stearate and the like are suitable antiadhesive and sliding agents. A suspension, syrup or elixir may be prepared as liquid oral compositions, which may contain water, glycols, oils, alcohols as well as coloring and flavouring agents.

Tablets may be prepared e.g. by compression following wet granulation. The mixture of the active ingredient with the carriers and optionally with a part of the disintegrating additive is granulated with an aqueous, alcoholic or aqueous-alcoholic solution of the binding agents in a suitable equipment, then the granulate is dried. Subsequently, after mixing the other disintegrating, sliding and anti-adhesive additives to the dried granulate, the mixture is compressed to tablets. If desired, the tablets may be provided with a groove in order to facilitate the administration. Tablets may also directly be prepared from a mixture containing the active ingredient and suitable additives. The compositions may optionally be transformed to dragée by employing the commonly used pharmaceutical additives, e.g. protective, flavouring or colouring agents such as sugar, cellulose derivatives (methyl- or ethylcellulose, carboxymethylcellulose sodium and the like), polyvinylpyrrolidone, calcium phosphate, calcium carbonate, food dyes, aromatizing agents or iron oxide pigments. Encapsulated compositions are prepared by filling a mixture of the active ingredient together with the additives into capsules.

For rectal administration the composition is formulated as a suppository containing a carrier mass (the so-called adeps pro suppositorio) in addition to the active ingredient. Vegetable fats such as hardened vegetable oils or triglycerides of $C_{12-18}$ fatty acids (preferably carriers commercialized under the trade name Witepsol) are useful carriers. The active ingredient is homogenized in the molten carrier mass and suppositories are prepared by pouring.

For parenteral administration the composition is formulated as an injectable preparation. For preparing an injectable solution, the active ingredients are dissolved in distilled water and/or various organic solvents, e.g. glycol ethers, optionally in the presence of solubilizing agents such as polyoxyethylene sorbitan monolaurate, -monooleate or -monostearate (Tween 20, Tween 60 or Tween 80, respectively). Besides, the injectable solution may contain various auxiliaries (additives), e.g. preservatives such as ethylenediamine tetraacetate and pH-adjusting and buffer substances as well as optionally a local anaesthetizing drug, e.g. lidocaine. Before filling into an ampoule, the injectable solution containing the pharmaceutical composition according to the invention is filtered and after filling it is sterilized.

The invention also relates to a method of treating Parkinson's disease, spastic rigid muscular hypertonicity, stroke, nervous system laesions, sclerosis multiplex, myclopathies, rachicele or articular pains. This method comprises administering a therapeutically effective amount of an active compound of formula (I) or a pharmaceutically acceptable acid addition salt thereof to the patient.

The invention is illustrated in detail by the following non-limiting Examples. The yields given in the Examples relate to compounds purified until reaching a constant melting point.

EXAMPLE 1

Preparation of chloromethyl-dimethyl-(4-fluorobenzyl)silane 10 ml of a previously prepared solvent mixture containing 60 ml of abs. benzene and 20 ml of abs. tetrahydrofuran are poured onto 3.16 g of magnesium shavings, then 0.2 ml of 1,2-dibromoethane is added to the mixture at 25° C. under nitrogen with exclusion of the air oxygen and moisture. The activation of magnesium is indicated by the liberation of ethylene gas bubbles. When the development of gas becomes intense, additional 50 ml of the above prepared solvent mixture are added, then a solution containing 14,46 g of 4-fluorobenzyl chloride, 5.2 g of 1,2-dibromoethane and 20 ml of the above-prepared and remained benzene/tetrahydrofuran solvent mixture are portionwise added at 26° C. The portionwise addition is carried out at a temperature between 24° C. and 26° C. during about 45 minutes. After addition the reaction mixture is cooled to 0° C., then heated to 30° C. and subsequently, 14.3 g of chlorochloromethyl-dimethylsilane are portionwise added to the heated mixture.

The temperature of the reaction mixture is maintained at 30° C. during the addition. Thereafter, the reaction mixture is stirred for additional 3 hours at room temperature. After termination of the reaction a solution of 6 g of ammonium chloride in 50 ml of water is added to the reaction mixture at a temperature not higher than 25° C. Then the mixture is separated, the benzene phase is extracted four times with a total of 120 ml of water and dried over anhydrous magnesium sulfate. After filtration of the solution the filtrate is evaporated to solvent-free to give 22 g of a pale yellow liquid residue which is the crude named product. This crude product is purified by distillation under reduced pressure to give the title compound in a yield of 19.8 g (90.8%) with a boiling point of 69°–71° C./0.5 torr.

EXAMPLE 2

Preparation of N-{[dimethyl-(4-fluorobenzyl)silyl]methyl}piperidine hydrochloride After adding 32.7 g of piperidine to a solution containing 32.5 g of chloromethyl-dimethyl-(4-fluorobenzyl)-silane in 40 ml of xylene, the reaction mixture is refluxed for 6 hours under stirring, then the precipitated piperidine hydrochloride is filtered at 20° C. and washed in 3 portions with a total of 60 ml of benzene. The filtrate is combined with the benzene washings and washed in 3 portions with a total of 150 ml of water and the organic phase is dried over anhydrous magnesium sulfate. After filtering the drying agent, the filtrate is evaporated to solvent-free to give the crude named compound as an oily liquid in the base form in a yield of 40 g. This crude product is purified by distillation under reduced pressure to give the title compound in a yield of 36.8 g (92%) with a boiling point of 97°–98° C./0.5 torr.

36.8 g of the base thus obtained are dissolved in 220 ml of methyl ethyl ketone and the solution is acidified to a pH of 4 to 5 by adding 20 ml of methanolic hydrogen chloride solution at a temperature below 25° C. 120 ml of the solution obtained are distilled off under atmospheric pressure, then the solution is cooled to 10° C. and filtered. The crystalline product named is washed 3 times with a total of 39 ml of methyl ethyl ketone at 0° C. and then dried to give the pure named compound in a yield of 38.9 g (93%), m.p.: 157.5°–158° C.

EXAMPLE 3

Preparation of N-{[dimethyl-(4-fluorobenzyl)silyl]methyl}morpholine hydrochloride Example 2 is followed, except that 32.6 g of morpholine are used as starting substance instead of 32.7 g of piperidine to obtain the named hydrochloride in a yield of 37 g (81%), m.p.: 176°–178° C.

EXAMPLE 4

Preparation of N-{[dimethyl-(4-fluorobenzyl)silyl]methyl}imidazole hydrochloride After dissolving 3.25 g of chloromethyl-dimethyl-(4-fluorobenzyl)silane in 10 ml of xylene, 2.55 g of imidazole are added to the solution which is then refluxed for 12 hours. After adding 50 ml of water to the mixture and separating, the organic phase is washed with a total of 100 ml of water in 5 portions. The organic phase is dried over anhydrous magnesium sulfate, filtered and the filtrate is evaporated to solvent-free. The pale yellow oily residue is dissolved in 20 ml of ethyl acetate and gaseous hydrogen chloride is introduced to the solution until reaching a pH value of 4 to 5. The precipitated crystalline title product named is filtered in two portions at 10° C. and washed with a total of 6 ml of ethyl acetate to give the named compound in a yield of 3.41 g (80%), m.p.: 152°–154° C.

EXAMPLE 5

Preparation of N-{[dimethyl-(4-fluorobenzyl)silyl]methyl}-2-methylimidazole

Example 4 is followed, except that 3.05 g of 2methylimidazole are employed as starting compound instead of 2.55 g of imidazole. The solvent-free base is recrystallized from methyl tertiary butyl ether to give the named compound in a yield of 7.75 g (70.2%), m.p.: 60°–62° C.

EXAMPLE 6

Preparation of
N-{[dimethyl-(4-fluorobenzyl)silyl]methyl}-piperazine dihydrochloride After adding 51.6 g of piperazine to the solution of 21.7 g of chloromethyl-dimethyl-(4-fluorobenzyl)silane in 100 ml of xylene the mixture is refluxed for 12 hours, then the mixture is poured into 300 ml of water and the phases are separated. The organic phase is washed 5 times with a total of 250 ml of water, dried over anhydrous sodium sulfate, filtered and the filtrate is evaporated to solvent-free. In this way the crude product named is obtained in the base form with a yield of 27 g, m.p.: 138°–140° C. (after recrystallization from methyl tert.-butyl ether).

The crude base is dissolved in 50 ml of isopropyl acetate and acidified to pH 1–2 by adding hydrogen chloride dissolved in isopropanol. The crystalline precipitate is filtered at 0° C., washed twice with a total of 10 ml of isopropyl acetate at 0° C. and then dried to give the named dihydrochloride product in a yield of 24 g (71.5%), m.p.: 190°–192° C.

EXAMPLE 7

Preparation of
$N^1$-{[dimethyl-(4-fluorobenzyl)silyl]methyl}-$N^4$-propionylpiperazine dihydrochloride After adding 5 ml of propionic anhydride to a solution containing 5.3 g of N-{[dimethyl-(4fluorobenzyl)silyl]methyl}-piperazine in 50 ml of toluene,the reaction mixture is refluxed for 6 hours, then cooled to room temperature and 100 ml of water as well as 10 ml of 20% sodium hydroxide solution are added. After vigorously stirring the reaction mixture for 15 minutes the organic phase is separated from the aqueous layer and washed twice with a total of 100 ml of water. The organic solution is dried over anhydrous magnesium sulfate and after filtration the filtrate is evaporated to solvent-free. The oily residue is dissolved in 50 ml of methyl ethyl ketone and the solution is acidified to pH 5.5 by adding methanolic hydrogen chloride solution. The crystalline precipitate is filtered at 0° C. and dried to obtain the named hydrochloride salt in a yield of 6.08 g (85%), m.p.: 188°–190° C.

EXAMPLE 8

Preparation of
$N^1$-n-butyl-$N^4$-{[dimethyl-(4-fluorobenzyl)silyl]methyl}piperazine dihydrochloride 6 g of powdered potassium carbonate and 5 g of n-butyl bromide are added to the solution of 5.3 g of N-{[dimethyl-(4-fluorobenzyl)silyl]methyl}piperazine in 50 ml of toluene, then the reaction mixture is refluxed for 12 hours. After termination of the reaction 100 ml of water are added and the phases are separated. The organic layer is washed twice with a total of 100 ml of water, dried over anhydrous magnesium sulfate and after filtration the filtrate is evaporated to solvent-free. The pale yellow oily residue is dissolved in 50 ml of methyl ethyl ketone and the solution is acidified to pH 1–2 by adding methanolic hydrogen chloride solution. The crystalline precipitate is filtered at 0° C. and washed twice with a total of 10 ml of cold methyl ethyl ketone. The named product is obtained in a yield of 7.15 g (90.5%), m.p.: 277°–279° C.

EXAMPLE 9

Preparation of
N-{[dimethyl-(4-fluorobenzyl)silyl]methyl}-1,2,4-triazole hydrochloride After adding 10 g of 1,2,4-triazole to 10.8 g of chloromethyl-dimethyl-(4-fluorobenzyl)silane dissolved in 50 ml of xylene, the reaction mixture is refluxed for 8 hours, then 200 ml of water are added and the phases are separated. The organic phase is washed 3 times with a total of 150 ml of water, dried over anhydrous magnesium sulfate and after filtration the filtrate is evaporated to solvent-free. The pale yellow oily residue is dissolved in 70 ml of methyl propyl ketone, the solution is acidified to pH 4.5 by adding methanolic hydrogen chloride solution and then concentrated to a volume of 40 ml by distillation under atmospheric pressure. The crystals precipitated are filtered at 0° C. to give the named product in a yield of 6.56 g (46%), m.p.: 113°–114° C.

EXAMPLE 10

Preparation of
N-{[dimethyl-(4-fluorobenzyl)silyl]methyl}-pyrrolidine hydrochloride Example 2 is followed, except that 27 g of pyrrolidine are used as starting substance instead of 32.7 g of piperidine. The title hydrochloride product is obtained in a yield of 35.8 g (83%), m.p.: 145°–146° C.

EXAMPLE 11

Preparation of
N-{[dimethyl-(4-fluorobenzyl)silyl]propyl}pyrrolidine hydrochloride A solution containing 12.2 of chloropropyldimethyl-(4-fluorobenzyl)silane and 8.9 g of pyrrolidine in 40 ml of benzene is refluxed for 15 hours, then cooled to room temperature and washed 5 times with a total of 150 ml of water. The organic layer is dried over anhydrous magnesium sulfate, filtered and the filtrate is evaporated to solvent-free. The pale yellow oily residue is dissolved in 40 ml of ether and the solution is acidified to pH 4.5 by adding an ethereal hydrogen chloride solution. The crystalline precipitate is filtered and dried to obtain the named hydrochloride salt in a yield of 13.7 g (87%), m.p.: 104°–105° C.

EXAMPLE 12

Preparation of
N-{[dimethyl-(4-fluorobenzyl)silyl]propyl}imidazole hydrochloride Example 11 is followed, except that 10.5 g of , imidazole are used as starting substance instead of 8.9 g of pyrrolidine. The named product is obtained in a yield of 13.2 g (80%), m.p.: 137°–138° C.

EXAMPLE 13

Preparation of
N-{[dimethyl-(4-fluorobenzyl)silyl]propyl}morpholine hydrochloride Example 11 is followed, except that 11 g of morpholine are used as starting substance instead of 8.9 g of pyrrolidine to obtain the title product in a yield of 14.7 g (89%), m.p.: 144°–146° C.

EXAMPLE 14

Preparation of
N-[(benzyldimethylsilyl)methyl]pyrrolidine
hydrochloride 9.9 g of chloromethyl-benzyl-dimethylsilane and 8.9 g of pyrrolidine are refluxed in 40 ml of xylene for 6 hours, then the reaction mixture is washed 5 times with a total of 250 ml of water at room temperature. The organic phase is dried over anhydrous magnesium sulfate, filtered and the filtrate is evaporated to solvent-free. The slightly yellow oily residue is dissolved in 20 ml of ethyl acetate and the solution is acidified to pH 4.5 by adding ethanolic hydrogen chloride solution. After drying the precipitate the named product is obtained in a yield of 11.3 g (94%), m.p.: 140°14 140.5° C.

EXAMPLE 15

Preparation of
N-[(benzyldimethylsilyl)methyl]piperidine
hydrochloride

Example 14 is followed, except that 10.5 g of piperidine are used as starting substance instead of 8.9 g of pyrrolidine. The named hydrochloride salt is obtained in a yield of 11.1 g (81%), m.p.: 190°–190.5° C.

EXAMPLE 16

Preparation of
N-[(benzyldimethylsilyl)methyl]imidazole
hydrochloride

Example 14 is followed, except that 10.2 g of imidazole are used as starting substance instead of 8.9 g of pyrrolidine. The named hydrochloride salt is obtained in a yield of 10.1 g (76%), m.p.: 150°–155° C.

EXAMPLE 17

Preparation of
N-[(benzyldimethylsilyl)methyl]-2-ethoxycarbonyl-
piperidine hydrochloride Example 14 is followed, except that 19.6 g of 2-ethoxycarbonylpiperidine are used as starting substance instead of 8.9 g of pyrrolidine to obtain the named product in a yield of 12.8 g (72%), m.p.: 135°–136° C.

EXAMPLE 18

Preparation of
$N^1$-[(benzyldimethylsilyl)methyl]-$N^4$-butylpiperazine
hydrochloride Example 14 is followed, except that 21 g of N-butylpiperazine are used as starting substance instead of 8.9 g of pyrrolidine and the solution is acidified to pH 1 (instead of pH 4.5) to give the named salt product in a yield of 13.5 g (75%), m.p. 209°–211° C.

EXAMPLE 19

Preparation of N
-[(benzyldimethylsilyl)propyl]piperidine hydrochloride

Example 12 is followed, except that 11.3 g of benzyl-chloropropyl-dimethylsilane are used as starting substance instead of 12.2 g of chloropropyl-dimethyl-(4-fluorobenzyl)silane. The named hydrochloride salt is obtained in a yield of 13.1 g (84%), m.p. 150°–152° C.

EXAMPLE 20

Preparation of
N-{[dimethyl-(4-methylbenzyl)silyl]methyl}piperazine
hydrochloride Example 15 is followed, except that 10.6 g of chloromethyl-dimethyl-(4-methylbenzyl)silane are used as starting substance instead of 9.9 g of benzyl-chloromethyl-dimethylsilane to obtain the named title product in a yield of 12.65 g (85%), m.p.: 188° C.

EXAMPLE 21

Preparation of
N-{[dimethyl-(4-methylbenzyl)silyl]methyl}pyrrolidine
hydrochloride Example 14 is followed, except that 10.6 g of chloromethyl-dimethyl-(4-methylbenzyl)silane are used as starting substance instead of 9.9 g of benzyl-chloromethyl-dimethylsilane to obtain the named product in a yield of 11.55 g (81%), m.p.: 128° C.

EXAMPLE 22

Preparation of
N-{[dimethyl-(4-ethylbenzyl)silyl]methyl}piperidine
hydrochloride Example 15 is followed, except that 11.3 g of chloromethyl-dimethyl-(4-ethylbenzyl)silane are used as starting substance instead of 9.9 g of benzyl-chloromethyl-dimethylsilane to give the named product in a yield of 19.55 g (85%), m.p.: 123°–125° C.

EXAMPLE 23

Preparation of
N-{[(4-chlorobenzyl)-dimethylsilyl]methyl}morpholine
hydrochloride A solution containing 11.15 g of (4-chlorobenzyl)-chloromethyl-dimethylsilane and 10.9 g of morpholine in 40 ml of toluene is refluxed for 9 hours, then cooled down and washed 5 times with a total of 250 ml of water. The organic phase is dried over anhydrous magnesium sulfate, filtered and evaporated to solvent-free. The pale yellow oily residue is dissolved in 40 ml of acetone and acidified to pH 4.5 by adding ethereal hydrogen chloride solution. The named product is obtained as a crystalline precipitate in a yield of 12.1 g (76%), m.p.: 208°–210° C.

EXAMPLE 24

Preparation of
N-{[(4-chlorobenzyl)-dimethylsilyl]methyl}piperazine
hydrochloride Example 23 is followed, except that 10.6 g of piperazine are used as starting substance instead of 10.9 g of morpholine to give the named product in a yield of 12.6 g (80%), m.p.: 162°–168° C.

EXAMPLE 25

Preparation of
$N^1$-butyl-$N^4$-{[(4-chlorobenzyl)dimethylsilyl]methyl}
piperazine hydrochloride Example 23 is followed, except that 21 g of N-butylpiperazine used as starting substance instead of 10.9 g morpholine and the solution is acidified to pH 1 (instead of pH 4.5). The named product is obtained in a yield of 14.6 g (71%), m.p.: 224°–227° C.

EXAMPLE 26

Preparation of
N-{[(4-chlorobenzyl)-dimethylsilyl]methyl}pyrrolidine
hydrochloride Example 23 is followed, except that 8.9 g pyrrolidine are used as starting substance instead of 10.9 g of morpholine to give the title product in a yield of 13 g (86%), m.p.: 135°–135° C.

EXAMPLE 27

Preparation of
N-{[dimethyl-(2-fluorobenzyl)silyl]methyl}piperidine
hydrochloride A solution containing 10.8 g of chloromethyldimethyl-(2-fluorobenzyl)silane and 10.6 g of piperidine in 40 ml of xylene is refluxed for 5.5 hours, then cooled down and washed 5 times with a total of 250 ml of water. After drying the organic phase over anhydrous magnesium sulfate and filtering off the drying agent, the filtrate is evaporated to solvent-free. The oily pale yellow residue is dissolved in 40 ml of methyl ethyl ketone and acidified to pH 4.5 by adding methanolic hydrogen chloride solution. 15 ml of solvent are distilled off from the solution under atmospheric pressure, the crystalline precipitate obtained is filtered at 0° C. and dried to give 13.1 g (87%) of the named product, m.p.: 203°–205° C.

EXAMPLE 28

Preparation of
N-{[dimethyl-(4-methoxybenzyl)silyl]methyl}piperidine hydrochloride Example 27 is followed, except that 11.4 g of chloromethyl dimethyl-(4-methoxybenzyl)silane are used as starting substance instead of 10.8 g of chloromethyl-dimethyl-(2-fluorobenzyl)silane. The named product is obtained in a yield of 13.2 g (84%), m.p.: 147°–148° C.

EXAMPLE 29

Preparation of N-{[dimethyl-(4-methoxybenzyl)silyl]methyl}pyrrolidine hydrochloride Example 28 is followed, except that 8.9 g of pyrrolidine are used as starting substance instead of 10.6 g of piperidine to obtain the named product in a yield of 13 g (87%), m.p.: 169° C.

EXAMPLE 30

Preparation of
N-{[(4-cyclohexylbenzyl)-dimethylsilyl]methyl}piperidine hydrochloride Example 27 is followed, except that 14.1 g of chloromethyl-(4-cyclohexylbenzyl)-dimethylsilane are used as starting substance instead of 10.8 g of chloromethyl-dimethyl-(2-difluorobenzyl)silane. The named product is obtained in a yield of 14.7 g (80%), m.p.: 187°–190° C.

EXAMPLE 31

Preparation of
N-{[(4-cyclohexylbenzyl)-dimethylsilyl]methyl}morpholine hydrochloride Example 30 is followed, except that 11 g of morpholine are used as starting substance instead of 10.6 g of piperidine. The named product is obtained in a yield of 15.1 g (82%), m.p.: 194°–196° C.

EXAMPLE 32

Preparation of
N-{[(4-cyclohexylbenzyl)-dimethylsilyl]methyl}pyrrolidine hydrochloride Example 30 is followed, except that 8.9 g of pyrrolidine are used as starting substance instead of 10.6 g of piperidine. The named product is obtained in a yield of 12.4 g (89%), m.p.: 178°–180° C.

EXAMPLE 33

Preparation of
$N^1$-butyl-$N^4$-{[(4-cyclohexylbenzyl)dimethylsilyl]methyl}piperazine hydrochloride Example 30 is followed, except that 21 g of N-butylpiperazine are used as starting substance instead of 10.6 g of piperidine and the solution is acidified to pH 1 (instead of pH 4.5). The named product is obtained in a yield 14.85 g (73%), m.p.: 272°–273° C.

EXAMPLE 34

Preparation of
N-([(2,4-dimethylbenzyl)dimethylsilyl]-piperidine
hydrochloride

Example 27 is followed, except that 11.3 g of chloromethyl-dimethyl-(2,4-dimethylbenzyl)silane are used as starting substance instead of 10.8 g of chloromethyl-dimethyl-(2-fluorobenzyl)silane. The named product is obtained in a yield of 13.55 (87%), m.p.: 133.5°–140° C.

EXAMPLE 35

Preparation of
N-{[(2-chloro-5-methylbenzyl)-dimethylsilyl]methyl}
piperidine hydrochloride Example 27 is followed, except that 12.35 g of chloromethyl-(2-chloro-5-methylbenzyl)dimethylsilane are used as starting substance instead of 10.8 of chloromethyldimethyl-(2-fluorobenzyl)silane to obtain the named product in a yield of 14.3 g (86%), m.p.: 162° C.

EXAMPLE 36

Preparation of
N-{[(2-chloro-3-methylbenzyl)-dimethylsilyl]methyl}
piperidine hydrochloride Example 27 is followed, except that 12,35 g of chloromethyl-(2-chloro-3-methylbenzyl)-dimethylsilane are used as starting substance instead of 10.8 g of chloromethyl-dimethyl-(2-fluorobenzyl)silane to give the named product in a yield of 13.5 g (81%), m.p.: 146°–148° C.

EXAMPLE 37

Preparation of
N-{[(2-chloro-3-methylbenzyl)-dimethylsilyl]methyl}
pyrrolidine hydrochloride Example 36 is followed, except that 8.9 g of pyrrolidine are used as starting substance instead of 10.6 g of piperidine. The named product is obtained in a yield of 13.2 g (83%), m.p.: 203.5°–205.5° C.

EXAMPLE 38

Preparation of
N-{[(2-chloro-4-methylbenzyl)-dimethylsilyl]methyl} piperidine hydrochloride Example 27 is followed, except that 12.35 g of chloromethyl-(2-chloro-4-methylbenzyl)dimethylsilane are used as starting substance instead of 10.8 of chloromethyl-dimethyl-(2-fluorobenzyl)silane. The named product is obtained in a yield of 14.3 g (86%), m.p.: 137°–138° C.

EXAMPLE 39

Preparation of
N-{[dimethyl-(2-fluoro-3-methylbenzyl)silyl]methyl} piperidine hydrochloride Example 27 is followed, except that 11.55 g of chloromethyl-dimethyl-(2-fluoro-3-methylbenzyl)silane are used as starting substance instead of 10.8 of chloromethyl-dimethyl-(2-fluorobenzyl)silane. The named product is obtained in a yield of 13.7 g (87%), m.p.: 188°–189° C.

EXAMPLE 40

Preparation of
N-{[dimethyl-(2-fluoro-4-methylbenzyl)silyl]methyl} piperidine hydrochloride Example 27 is followed, except that 11.5 g of chloromethyl-dimethyl-(2-fluoro-3-methylbenzyl)silane are used as starting substance instead of 10.8 of chloromethyl-dimethyl-(2-fluorobenzyl)silane. The named product is obtained in a yield of 13.2 g (83.8%), m.p.: 116°–118° C.

EXAMPLE 41

Preparation of
N-{[dimethyl-(2-fluoro-5-methylbenzyl)silyl]methyl} piperidine hydrochloride Example 27 is followed, except that 11.5 g of chloromethyl-dimethyl-(2 -fluoro-5-methylbenzyl)silane are used as starting substance instead of 10.8 of chloromethyl-dimethyl-(2-fluorobenzyl)silane. The named product is obtained in a yield of 13.3 g (84.2%), m.p.: 157°–160° C.

EXAMPLE 42

Preparation of
N-{[dimethyl-(2-fluoro-5-methoxybenzyl)silyl]methyl} piperidine hydrochloride Example 27 is followed, except that 12.3 g of chloromethyl-dimethyl-(2-fluoro-5-methoxybenzyl)silane are used as starting substance instead of 10.8 of chloromethyl-dimethyl-(2-fluorobenzyl)silane. The named product is obtained in a yield of 14.3 g (86.2%), m.p.: 145°–147° C.

EXAMPLE 43

Preparation of
N-{[dimethyl-(2-fluoro-4-methoxybenzyl)silyl]methyl} piperidine hydrochloride Example 27 is followed, except that 12.3 g of chloromethyl-dimethyl-(2-fluoro-4-methoxybenzyl)silane are used as starting substance instead of 10.8 of chloromethyl-dimethyl-(2-fluorobenzyl)silane. The named product is obtained in a yield of 14 g (85%), m.p.: 240°–241° C.

We claim:

1. A method of treating a mammalian subject for Parkinson's disease or to provide a central muscle relaxant effect, which comprises the step of administering to said mammalian subject in need of said treatment, a therapeutically effective amount of a compound of the Formula (I)

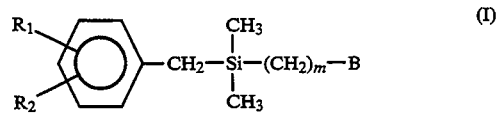

wherein
m is 1, 2 or 3;
$R_1$ and $R_2$ each independently stand for hydrogen, $C_1$ to $C_4$, straight or branched chain alkyl, $C_1$ to $C_4$ alkoxy, $C_5$ to $C_7$ cycloalkyl, or halogen; and
B is a 5- or 6-membered saturated or unsaturated heterocyclic group containing a nitrogen heteroatom, said heterocyclic group being bound through its heterocyclic nitrogen atom to the remainder of the compound, and which is selected from the group which consists of N-piperidino, N-imidazolyl, N-(2-methyl)-imidazolyl, N-piperazino, N-(4-propionyl)-piperazino, N-(4-n-butyl)-piperazino, N-1,2,4-triazolyl), N-pyrrolidino, N-morpholino, and (2-ethoxycarbonyl)-N-piperidino; or a pharmaceutically acceptable salt thereof.

2. The method of treating a mammalian subject for Parkinson's disease or to provide a central muscle relaxant effect defined in claim 1 where the compound of the Formula (I) is selected from the group consisting of:

N-{[dimethyl-(4-fluorobenzyl)silyl]methyl}piperidine;
N-{[dimethyl-(4-fluorobenzyl)silyl]methyl}pyrrolidine;
N-[benzyl-dimethylsilyl)propyl]piperidine;
N-{[dimethyl-(2,4-dimethylbenzyl)silyl]methyl}piperidine;
N-{[(2-chloro-5-methylbenzyl)-dimethylsilyl]methyl} piperidine;
N-{[dimethyl-(4-fluorobenzyl)silyl]propyl}pyrrolidine; and
N-{[dimethyl-(4-fluorobenzyl)silyl]propyl}imidazole;
or a pharmaceutically acceptable salt thereof.

3. The method of treating a mammalian subject for Parkinson's disease or to provide a central muscle relaxant effect defined in claim 1 where the compound of the Formula (I) is N-{[dimethyl-(4-fluorobenzyl)silyl]methyl}-piperidine, or a pharmaceutically acceptable salt thereof.

* * * * *

UNITED STATES PATENT AND TRADEMARK OFFICE
CERTIFICATE OF CORRECTION

PATENT NO. : 5,340,823
DATED : August 23, 1994
INVENTOR(S) : Sandor FARKAS et al It is certified that error appears in the above-identified patent and that said Letters Patent is hereby corrected as shown below:

On the title page, item [75] in the name of the eighth inventor for "Szilvia Petűfi-Vass" read -- Szilvia Petofi-Vass --.

Signed and Sealed this

Twentieth Day of December, 1994

*Attest:*

BRUCE LEHMAN

*Attesting Officer*   *Commissioner of Patents and Trademarks*